United States Patent
Zhou et al.

(10) Patent No.: US 11,921,029 B2
(45) Date of Patent: Mar. 5, 2024

(54) PRODUCT INDEX MECHANISM AND PRODUCT INSPECTION SYSTEM

(71) Applicants: Tyco Electronics (Shanghai) Co., Ltd., Shanghai (CN); TE Connectivity Services GmbH, Schaffhausen (CH)

(72) Inventors: Lei (Alex) Zhou, Shanghai (CN); Dandan (Emily) Zhang, Shanghai (CN); Roberto Francisco-Yi Lu, Bellevue, WA (US); Lvhai (Samuel) Hu, Shanghai (CN); Qing (Carrie) Zhou, Shanghai (CN); Rong Zhang, Shanghai (CN)

(73) Assignees: Tyco Electronics (Shanghai) Co., Ltd., Shanghai (CN); TE Connectivity Solutions GmbH, Schaffhausen (CH)

( * ) Notice: Subject to any disclaimer, the term of this patent is extended or adjusted under 35 U.S.C. 154(b) by 177 days.

(21) Appl. No.: 17/689,674

(22) Filed: Mar. 8, 2022

(65) Prior Publication Data
US 2022/0291115 A1     Sep. 15, 2022

(30) Foreign Application Priority Data
Mar. 9, 2021   (CN) .......................... 202110257266.4

(51) Int. Cl.
*G01N 19/08*     (2006.01)

(52) U.S. Cl.
CPC .................................. *G01N 19/08* (2013.01)

(58) Field of Classification Search
CPC ...................................................... G01N 19/08
See application file for complete search history.

(56) References Cited

FOREIGN PATENT DOCUMENTS

| CN | 210773927 U | * | 6/2020 |
| CN | 214190259 U | * | 9/2021 |
| CN | 114216848 A | * | 3/2022 |
| CN | 116135749 A | * | 5/2023 |

* cited by examiner

*Primary Examiner* — Jamel E Williams
(74) *Attorney, Agent, or Firm* — Barley Snyder

(57) ABSTRACT

A product index mechanism for a product inspection system includes a material strip driving wheel and an index structure driving wheel. The material strip driving wheel engages with a material strip carrying a plurality of products to be inspected by an inspection device of the product inspection system. The driving wheel drives the material strip to move. The index structure driving wheel rotates synchronously with the material strip driving wheel and includes a plurality of product index structures thereon. As a product on the material strip is moved by the material strip driving wheel to an inspection position of the inspection device, one product index structure on the index structure driving wheel is rotated to a trigger position corresponding to a trigger of the inspection system. Activation of the trigger transmits a trigger signal to the inspection device to inspect the product.

20 Claims, 4 Drawing Sheets

PRODUCT INDEX MECHANISM AND PRODUCT INSPECTION SYSTEM

CROSS-REFERENCE TO RELATED APPLICATIONS

This application claims the benefit of Chinese Patent Application No. 202110257266.4 filed on Mar. 9, 2021 in the China National Intellectual Property Administration, the whole disclosure of which is incorporated herein by reference.

FIELD OF THE INVENTION

The present disclosure generally relates to the field of product detection, and more particularly, to a product index mechanism and a product inspection system including the product index mechanism suitable for the inspection of material strip products with different specifications.

BACKGROUND

In industrial production, it is usually necessary to check various products to determine whether they are qualified. Examples of products may include, for example, press formed strip terminals, such as conductive terminals for electrical connectors.

Usually, products have different specifications. As an example, the product material strip shown in FIG. 1 is formed by stamping, including the material strip 1 and the product 2 carried thereon. The material strip 1 is provided with positioning holes 11, and the conveying mechanism engages the positioning holes 11 to drive the material strip 1 and the product 2 carried thereon to move through the inspection device for inspection. FIG. 1 shows various types or different specifications of material strips, for example, the material strip with positioning holes 11 one-to-one corresponding to products 2 (see the material strip shown in (a) in FIG. 1), the material strip with positioning holes 11 not one-to-one corresponding to products 2, such as the material strip with positioning holes 11 corresponding to or aligned with only part of products 2 (see the material strip shown in (b) in FIG. 1). A material strip on which the positioning holes 11 and the products 2 are misaligned or offset (see the material strip shown in (c) and (d) in FIG. 1), a material strip with irregular spacing between the positioning holes 11 and/or the products 2 (see the material strip shown in (d) in FIG. 1), etc.

Conventional product detection systems can only detect or adapt to a single specification of product, have poor detection flexibility, and require significant time and energy on product positioning to ensure that the inspection device can detect the corresponding product, which reduces the inspection speed.

SUMMARY

According to an embodiment of the present disclosure, a product index mechanism for a product inspection system includes a material strip driving wheel and an index structure driving wheel. The material strip driving wheel is connected to a material strip carrying a plurality of products to be inspected by an inspection device of the product inspection system. The driving wheel is driven to rotate to drive the material strip to move. The index structure driving wheel rotates synchronously with the material strip driving wheel and includes with a plurality of product index structures thereon. As a product on the material strip is moved by the material strip driving wheel to an inspection position of the inspection device, one product index structure on the index structure driving wheel is rotated to a trigger position corresponding to a trigger of the inspection system. Activation of the trigger transmits a trigger signal to the inspection device to inspect the product.

BRIEF DESCRIPTION OF THE DRAWINGS

The invention will now be described by way of example with reference to the accompanying Figures, of which.

DETAILED DESCRIPTION OF THE EMBODIMENTS

Figure 1:
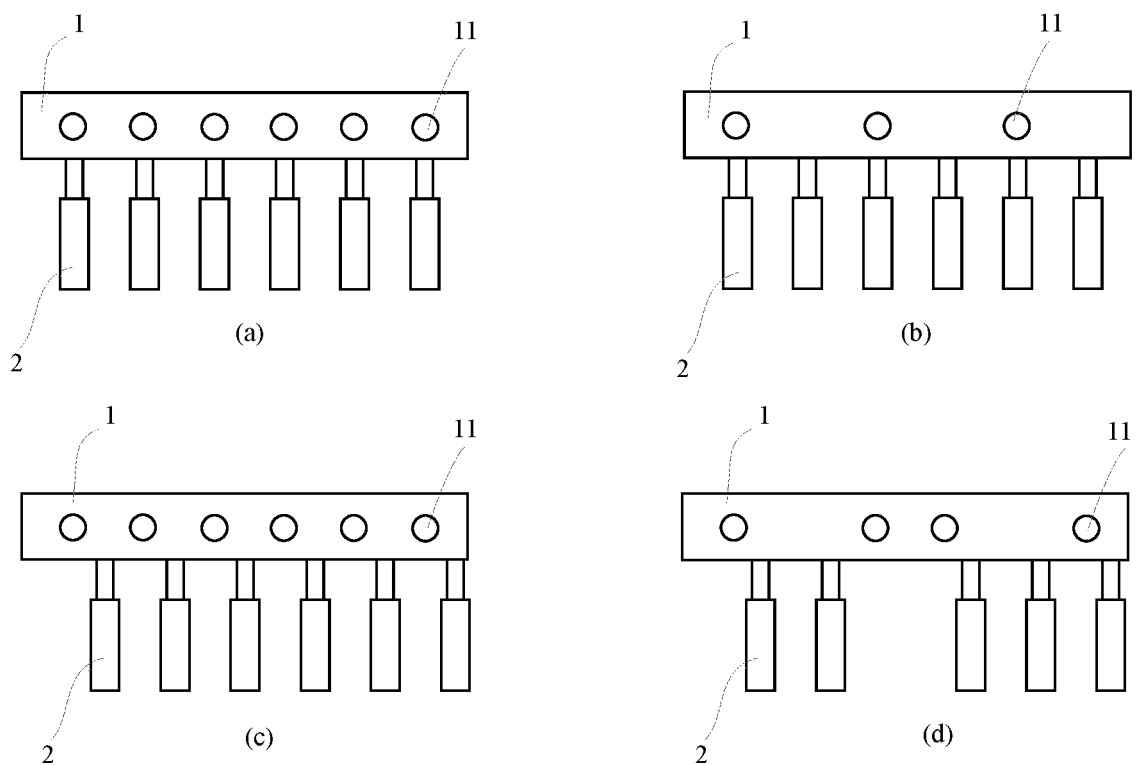
FIG. 1 is a schematic view showing various types of product material strips.

Exemplary embodiments of the present disclosure will be described hereinafter in detail with reference to the attached drawings, wherein the like reference numerals refer to the like elements. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

According to an embodiment of the present disclosure, a product index mechanism for a product inspection system includes an inspection device for inspecting a plurality of products on a material strip and a trigger configured to send a trigger signal to the inspection device for triggering the inspection device to inspect the products on the material strip. The product index mechanism includes a material strip driving wheel connected with the material strip and driven to rotate to drive the material strip to move, and an index structure driving wheel rotating synchronously with the material strip driving wheel and provided with a plurality of product index structures thereon. When one product on the material strip is moved by the material strip driving wheel to an inspection position of the inspection device, one product index structure on the index structure driving wheel is rotated to a trigger position corresponding to the trigger to trigger the trigger to send the trigger signal to the inspection device.

According to an exemplary embodiment of the present disclosure, a product index mechanism is provided, which is suitable for positioning or addressing a plurality of products 2 on the material strip 1, so that the inspection device 140 of the product inspection system can accurately inspect the products and avoid missed or wrong inspection. As an example, the material strip may be a stamped material strip, and the product may be a terminal stamped on the material strip, such as a conductive terminal. The inspection device 140 may include a visual inspection device, such as a camera.

Figure 2:
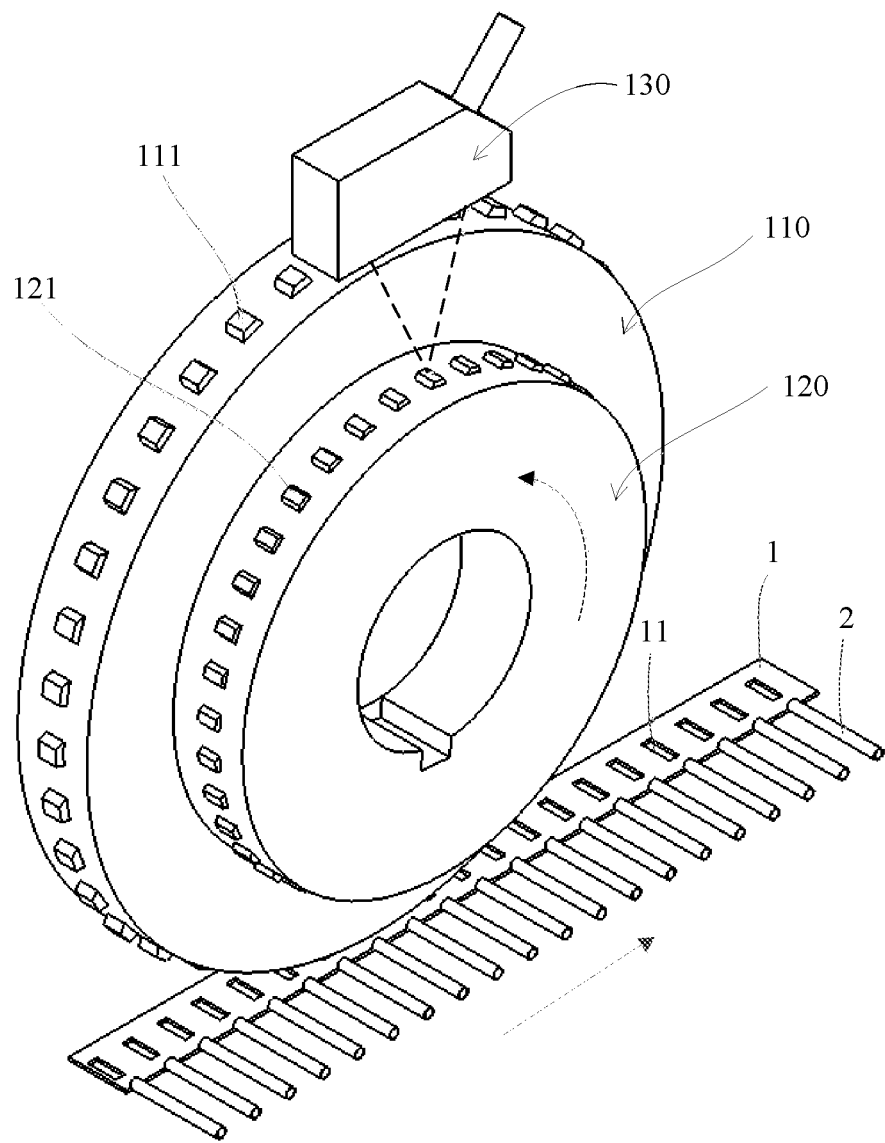
FIG. 2 is an illustrative perspective view of a product index mechanism according to an exemplary embodiment of the present disclosure.
Figure 3:
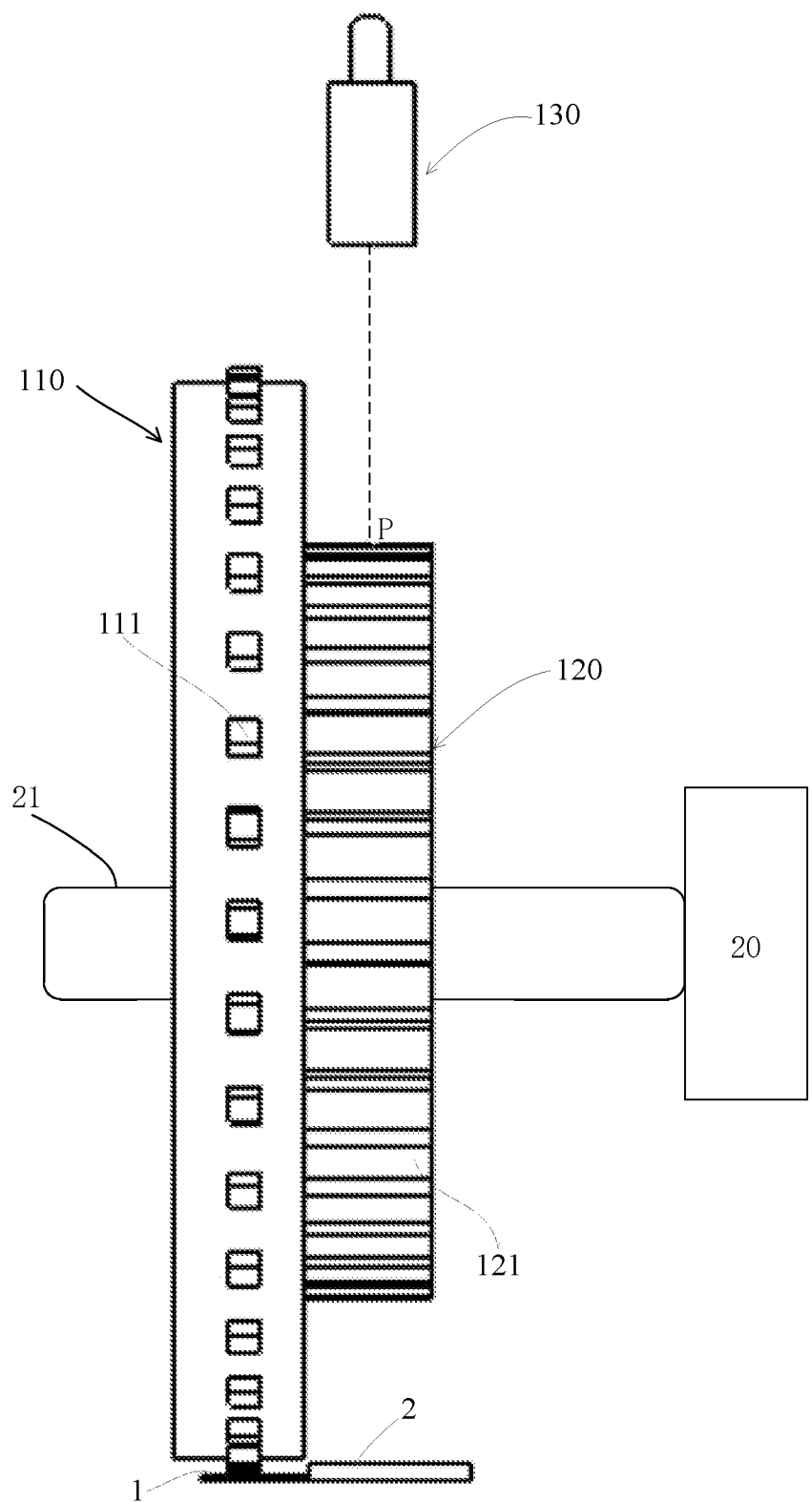
FIG. 3 is an illustrative side view of a product index mechanism according to an exemplary embodiment of the present disclosure.
Figure 4:
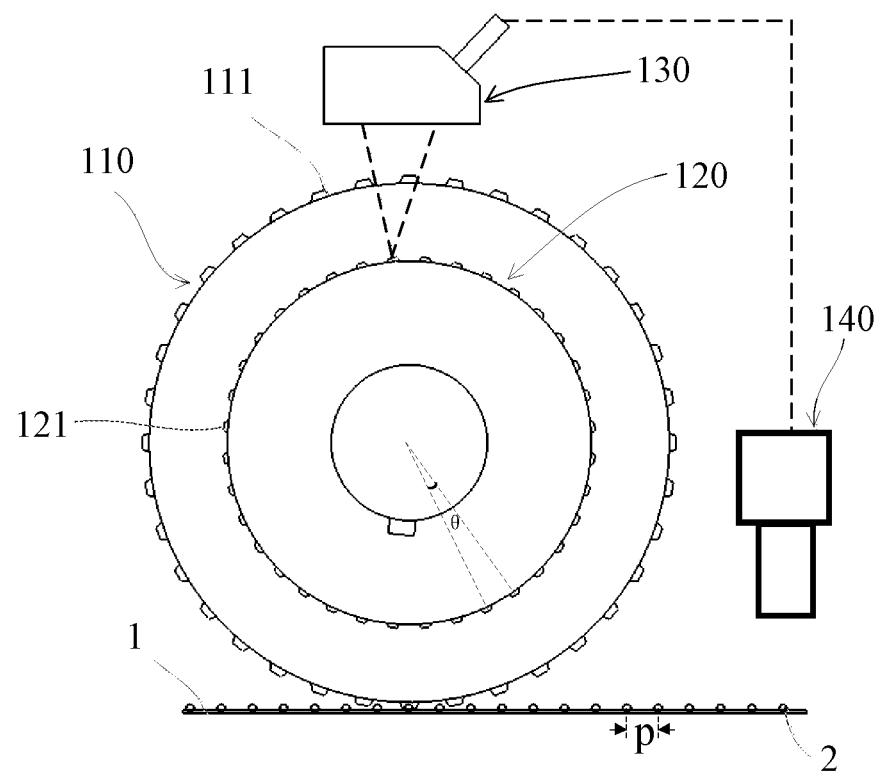
FIG. 4 is an illustrative side view of a product inspection system including the product index mechanism according to an exemplary embodiment of the present disclosure.

In the exemplary embodiment, as shown in FIGS. 2-4, the product index mechanism includes a material strip driving wheel 110 and an index structure driving wheel 120, the material strip driving wheel 110 is used to connect with the material strip 1 and can rotate to drive the material strip 1 to move, and the index structure driving wheel 120 is arranged to rotate synchronously with the material strip driving wheel 110. The index structure driving wheel 120 is provided with a plurality of product index structures 121. After the initial configuration, that is, after the material strip driving wheel and the index structure driving wheel are installed in place, the product index structures 121 corresponds to a plurality of products 2 on the material strip 1 to be inspected for positioning or addressing the products 2, that is, the positioning of the products 2 relative to the inspection device 140 can be determined through the product index structures 121, to ensure that the inspection device 140 accurately checks the product. The product inspection system also includes a trigger 130 for sending a trigger signal to the inspection device 140 to trigger the inspection device 140 to inspect the product on the material belt.

The trigger position P corresponding to the trigger 130 of the product inspection system is set or selected for the index structure drive wheel 120, for example, the trigger position P is aligned with the trigger 130 on the index structure drive wheel 120. For example, as shown in the figure, when the product index structures 121 are arranged on the peripheral surface of the index structure driving wheel 120, the selected trigger position P is located on the peripheral surface of the index structure driving wheel 120 opposite to the trigger 130. It will be understood that although the specific part on the index structure driving wheel as the trigger position changes during the rotation of the index structure driving wheel, the positioning of the trigger position relative to the trigger 130 is fixed. In other embodiments, the product index structures may be arranged on one of the two opposite wheel surfaces of the index structure driving wheel.

As an example, the trigger 130 of the product inspection system may include a sensor for detecting whether there is a product index structure 121 at the trigger position P. When it is detected that there is a product index structure 121 at the trigger position P, a trigger signal is sent to the inspection device 140 to trigger the inspection device 140 to start inspecting a corresponding product 2 on the material strip 1.

Each product index structure 121 can be rotated to the trigger position P, that is, through the rotation of the index structure driving wheel 120, each product index structure 121 can be rotated to the trigger position P. The existence of the product index structure at the trigger position causes the trigger 130 to trigger the inspection device 140 to inspect the product 2 on the material strip 1.

According to the embodiment of the present disclosure, while the material strip driving wheel 110 drives a product 2 on the material strip 1 to the inspection position of the inspection device 140, the index structure driving wheel 120 rotates a corresponding product index structure 121 to the trigger position P corresponding to the trigger 130 to trigger the trigger 130 through the product index structure 121 at the trigger position, thus sending a trigger signal to the inspection device 140. The inspection device causes the start the inspection of the product reaching the inspection position of the inspection device 140. For example, a plurality of product index structures 121 on the index structure driving wheel 120 are arranged so that when each product index structure 121 is rotated to the trigger position P, one product 2 on the material strip 1 driven by the material strip driving wheel 110 rotating synchronously with the index structure driving wheel 120 is moved to the inspection position of the inspection device 140 (such as within the field of view of the inspection device, such as at the focus position of the camera) and is inspected by the inspection device 140.

For example, a plurality of product index structures 121 may be formed on the peripheral surface of the index structure drive wheel 120 at intervals. As an example, the product index structures 121 may include protrusions, ridges, teeth, recesses, stripe patterns, marking symbols, and the like that can be sensed by the trigger 130, such as a sensor. Therefore, the trigger position can also be understood as the position of sensing the product index structure by the trigger (such as a sensor).

According to an embodiment of the present disclosure, a circumferential spacing or angular spacing θ between adjacent product index structures 121 corresponding to a first spacing p between adjacent products on the material strip. When each product index structure 121 rotates an angle corresponding to the circumferential spacing or angular spacing, the corresponding product 2 on the material strip 1 driven by the material strip drive wheel 110 moves a distance equal to the first spacing p and is thus located at the inspection position of the inspection device 140.

In one example, the first product index structure 121 is located upstream of the trigger position P in the rotation direction and the first product 2 located upstream of the inspection position of the inspection device 140 in the material strip movement direction. The index structure in the product index structure 121 is rotated to the trigger position P (such as the position facing or aligned with the trigger 130) due to the rotation angle θ of the index structure driving wheel 120, the product 2 driven by the material strip drive wheel 110 is just moved a distance equal to the first spacing p to the inspection position of the inspection device 140, so as to accept the inspection of the inspection device 140. It can be understood that the circumferential spacing or angular spacing between product index structures will vary according to the product spacing on the material strip. The inspection device can be set at any suitable position, such as before or after the product index mechanism.

In the illustrated embodiment, as shown in FIGS. 1 and 2, the index structure driving wheel 120 and the material strip driving wheel 110 are coaxially arranged side by side, and the index structure driving wheel 120 may be arranged on one side of the material strip driving wheel 110 close to the product 2 on the material strip 1. In other embodiments, depending on the position of the trigger, the index structure drive wheel may be arranged at other positions, such as on the side of the material strip drive wheel away from the product on the material strip. The diameter of the index structure driving wheel 120 may be smaller than the diameter of the material strip driving wheel 110 so that when the material strip driving wheel 110 engages the material strip 1, the index structure driving wheel 120 is separated from the products 2 on the material strip 1. The material strip drive wheel 110 is provided with engaging structures 111, such as protrusions, for engaging the positioning holes 11 on the material strip 1 to drive the material strip 1 to move. The engaging structures 111 may be arranged on the outer peripheral surface of the material strip drive wheel 110, and the circumferential spacing or angular spacing θ between the engaging structures 111 may be corresponds to the spacing between the positioning holes 11 on the material strip 1. As an example, the material strip drive wheel and/or the index structure drive wheel may include a ratchet.

In an example, the index structure driving wheel may be formed integrally with the material strip driving wheel, or the index structure driving wheel may be detachably mounted to the material strip driving wheel, or the index structure driving wheel may be arranged separately from the material strip driving wheel.

The product inspection system may be provided with a driving mechanism that drives the material strip driving wheel 110 and the index structure driving wheel 120 to rotate synchronously. It can be understood that the material strip driving wheel and the index structure driving wheel can be driven and rotated by the same driving mechanism or synchronously driven by different driving mechanisms. For example, in the embodiment illustrated in FIG. 4, the drive mechanism includes a motor 20 that drives the material strip drive wheel 110 and the index structure drive wheel 120 to rotate synchronously by inserting a rotating shaft 21 passing through the material strip drive wheel 110 and the index structure drive wheel 120.

The product inspection system according to the exemplary embodiment of the present disclosure is provided with the above product index mechanism, which corresponds to the material strip to be inspected and helps to determine the position of the products on the material strip, so that the inspection device can accurately inspect the product.

Therefore, the product inspection system according to the embodiment of the present disclosure is suitable for inspecting a variety of types of material strips with a variety of product spacings, and includes or is equipped with a plurality of replaceable index structure driving wheels, each of which corresponds to a type of material strip with a product spacing. When each product index structure of the index structure driving wheel is rotated to the trigger position corresponding to the trigger, one product on the corresponding type of material strip is in the inspection position of the inspection device. When checking a type of material strip, select and arrange a suitable index structure driving wheel according to the arrangement of the products on the material strip, for example, according to the product spacing on the material strip, so that the arrangement of the product index structure corresponds to the products on the material strip. During initial installation and configuration, at least the index structure driving wheel is arranged so that one product index mechanism is located at the trigger position corresponding to the trigger, and one product on the material strip is located at the inspection position of the inspection device.

Various types of material strips may have different positioning hole spacings, so the product inspection system may also include or be equipped with a plurality of replaceable material strip driving wheels, each if which is suitable for engaging a type of material strip with a positioning hole spacing.

Thus, the product inspection system according to the embodiment of the present disclosure can quickly replace the product index mechanism, or replace the corresponding material strip driving wheel and/or index structure driving wheel when inspecting different types of material strips, so as to accurately locate the product and increase the inspection speed.

In addition, those areas in which it is believed that those of ordinary skill in the art are familiar, have not been described herein in order not to unnecessarily obscure the invention described. Accordingly, it has to be understood that the invention is not to be limited by the specific illustrative embodiments, but only by the scope of the appended claims.

It should be appreciated for those skilled in this art that the above embodiments are intended to be illustrated, and not restrictive. For example, many modifications may be made to the above embodiments by those skilled in this art, and various features described in different embodiments may be freely combined with each other without conflicting in configuration or principle.

Although several exemplary embodiments have been shown and described, it would be appreciated by those skilled in the art that various changes or modifications may be made in these embodiments without departing from the principles and spirit of the disclosure, the scope of which is defined in the claims and their equivalents.

As used herein, an element recited in the singular and proceeded with the word "a" or "an" should be understood as not excluding plural of the elements or steps, unless such exclusion is explicitly stated. Furthermore, references to "one embodiment" of the present disclosure are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

What is claimed is:

1. A product index mechanism for a product inspection system, comprising:
    a material strip driving wheel sized to engage with a material strip carrying a plurality of products to be inspected by an inspection device of the product inspection system, the driving wheel driven to rotate to drive the material strip to move; and
    an index structure driving wheel rotating synchronously with the material strip driving wheel and including plurality of product index structures thereon, as a product on the material strip is moved by the material strip driving wheel to an inspection position of the inspection device, one product index structure on the index structure driving wheel is rotated to a trigger position corresponding to a trigger of the inspection system to activate the trigger to transmit a trigger signal to the inspection device to inspect the product.

2. The product index mechanism according to claim 1, wherein the plurality of product index structures are spaced from each other on a peripheral surface of the index structure driving wheel.

3. The product index mechanism according to claim 1, wherein an angular spacing between two adjacent product index structures corresponds to a first spacing between two adjacent products to be inspected on the material strip.

4. The product index mechanism according to claim 3, wherein in response to the product index structure rotated an angle corresponding to the angular spacing, the product on the material strip driven by the material strip driving wheel is moved a distance equal to the first spacing.

5. The product index mechanism according to claim 2, wherein the plurality of product index structures include at least one of protrusions, ridges, recesses, stripe patterns or marking symbols arranged on the peripheral surface of the index structure driving wheel and capable of being sensed by the trigger.

6. The product index mechanism according to claim 1, wherein the indexing structure driving wheel and the material strip driving wheel are coaxially arranged side by side.

7. The product index mechanism according to claim 6, wherein a diameter of the indexing structure driving wheel is smaller than that of the material strip driving wheel.

8. The product index mechanism according to claim 1, wherein the index structure driving wheel is formed integrally with the material strip driving wheel.

9. The product index mechanism according to claim 1, wherein the index structure driving wheel is detachably mounted to the material strip driving wheel.

10. The product index mechanism according to claim 1, wherein the material strip includes positioning holes, and the material strip driving wheel is provided with engagement structures for engaging with the positioning holes to drive the material strip to move.

11. The product index mechanism according to claim 1, wherein at least one of the material strip driving wheel or the indexing structure driving wheel includes a ratchet.

12. A product inspection system for inspecting a plurality of products on a material strip, comprising:
    an inspection device inspecting a plurality of products on a material strip;
    a trigger sending a trigger signal to the inspection device for triggering the inspection device to inspect the products on the material strip; and
    a product index mechanism of a product inspection system, comprising:
        a material strip driving wheel adapted to connect with the material strip and driven to rotate to drive the material strip to move; and
        an index structure driving wheel rotating synchronously with the material strip driving wheel and including a plurality of product index structures thereon, when one product on the material strip is moved by the material strip driving wheel to an inspection position of the inspection device, one product index structure on the index structure driving wheel is rotated to a trigger position corresponding to the trigger to activate the trigger to send the trigger signal to the inspection device.

13. The product inspection system according to claim 12, wherein the product inspection system includes a plurality of replaceable index structure driving wheels, and each index structure driving wheel corresponds to a type of a plurality of material strips with a product spacing.

14. The product inspection system according to claim 13, wherein when one product index structure on the index structure driving wheel is rotated to the trigger position, one product on the corresponding type of material strip is moved to the inspection position of the inspection device.

15. The product inspection system according to claim 13, wherein the plurality of types of material strips have different positioning hole spacings, and the product inspection system further comprises a plurality of replaceable material strip driving wheels, and each material strip driving wheel is suitable for engaging one type of material strip with a positioning hole spacing.

16. The product inspection system according to claim 12, wherein the trigger includes a sensor detecting whether a product index structure exists at the trigger position.

17. The product inspection system according to claim 16, wherein if the sensor detects that a product index structure exists at the trigger position, the sensor sends a trigger signal to the inspection device, so as to trigger the inspection device to inspect a corresponding product on the material strip.

18. The product inspection system according to claim 12, wherein the trigger is positioned opposite to the trigger position.

19. The product inspection system according to claim 12, further comprising a driving mechanism for driving the material strip driving wheel and the index structure driving wheel to rotate synchronously.

20. The product inspection system according to claim 12, wherein at least one of the material strip driving wheel or the indexing structure driving wheel includes a ratchet.

* * * * *